United States Patent [19]
Johannsen

[11] Patent Number: 4,730,400
[45] Date of Patent: Mar. 15, 1988

[54] DRUM REACTOR FOR MANUFACTURING FERTILIZERS AND OTHER RAW MATERIALS BY AEROBIC FERMENTATION

[76] Inventor: Gunter Johannsen, Bahnweg 3, 2178 Otterndorf, Fed. Rep. of Germany

[21] Appl. No.: 807,015

[22] Filed: Dec. 9, 1985

[51] Int. Cl.⁴ .................. F26B 3/04; F26B 17/32
[52] U.S. Cl. .............................. 34/12; 34/33; 34/56; 34/135; 34/141
[58] Field of Search ............. 34/12, 126, 135, 141, 34/142, 56, 33; 71/9; 432/117

[56] References Cited

U.S. PATENT DOCUMENTS

| | | | |
|---|---|---|---|
| 2,264,646 | 12/1941 | Spears. | |
| 3,055,744 | 9/1962 | Petersen | 71/9 |
| 3,096,172 | 7/1963 | Zimmerley et al. | 432/117 |
| 3,398,458 | 8/1968 | Quanquin et al. | 34/135 |
| 3,401,923 | 9/1968 | Bearce | 34/126 |
| 3,533,775 | 10/1970 | Brown | 71/9 |
| 3,756,784 | 9/1973 | Pittwood | 71/9 |
| 4,127,388 | 11/1978 | Maczko et al. | 34/135 |
| 4,307,520 | 12/1981 | Lutz | 34/135 |

FOREIGN PATENT DOCUMENTS

| | | |
|---|---|---|
| 70654 | 2/1892 | Fed. Rep. of Germany. |
| 202685 | 8/1907 | Fed. Rep. of Germany. |
| 1033684 | 7/1958 | Fed. Rep. of Germany. |
| 2026728 | 11/1975 | Fed. Rep. of Germany. |
| 3134084 | 3/1983 | Fed. Rep. of Germany. |

Primary Examiner—Larry I. Schwartz
Attorney, Agent, or Firm—Birch, Stewart, Kolasch & Birch

[57] ABSTRACT

Drum reactor (10) for aerobic fermentation has a frame (12) with which a height adjusting device (14). The drum reactor is provided with a rotary drum (11) having air pipes (20) extending longitudinally along its outer shell. The air pipes (20) are subject to compressed air and humidity by the action of a distributor slide valve (25) so that the air pipe (37) which is free of fermenting material (26) is inactive. Associated with the air pipes (20) are a plurality of jets (21) which lead into the drum interior (27) where they are at least partially covered by baffles (22). By their plough-like disposition, the baffles ensure circulation and onwards conveyance of the material to be fermented. Provided on the drum bottom (38) is a discharge orifice (33) which can be closed by a plough flap (36). For delivery of fermented material, the plough flap can be spread open into the drum interior.

18 Claims, 9 Drawing Figures

DRUM REACTOR FOR MANUFACTURING FERTILIZERS AND OTHER RAW MATERIALS BY AEROBIC FERMENTATION

BACKGROUND OF THE INVENTION

The invention relates to a drum reactor for the manufacture of fertilisers and other raw materials from waste arising from animal husbandry, plant residues and other fermentable raw materials by aerobic fermentation, and having a drivable obliquely positioned rotary drum to hold the material to be fermented, and having an arrangement of air pipes with jets leading into the interior for blowing air into the rotary drum and comprising a feeder funnel disposed above the drum.

Such a drum reactor is known from German Patent Specification No. 20 26 728 and serves to process waste materials by fermentation to reproduce reusable products, for example fertilisers. For this purpose, the material to be fermented is poured into the drum reactor and subjected to the action of water and compressed air. With the onset of fermentation, gases and heat are generated which must be dissipated. The oxygen needed for this organic conversion process is carried in together with the air introduced under a slight over-pressure into the free space above the material to be fermented.

In the case of another apparatus such as is known from German Patent Specification No. 1 033 684, only the feed line is opened up which is located in the bottom part of the container while it is rotating, in other words the part in which the material to be fermented is contained.

With the prior art, there is on the one hand the danger of the oxygen not coming into sufficiently intimate contact with the material to be fermented and on the other that the material to be fermented which comprises a relatively low rate of permeability to air, will clog the air jets.

SUMMARY OF THE INVENTION

The object of the present invention is to provide a drum reactor of the type described at the outset but which permits of even ventilation of the material to be fermented and which avoids the danger of the air inlet apertures becoming clogged.

This problem is resolved in that the arrangement of air pipes is constituted by a plurality of air pipes distributed over the periphery of and extending longitudianlly on the rotary drum, the jets leading into the interior of the drum being a least in some cases covered by baffles. These measures provide a drum reactor in which during one rotation of the drum the material to be fermented is kept in constant movement and is loosened-up by the baffles which act rather like a plough. The air needed for a constantly adequately good ventilation can be blown through the plurality of air pipes directly into the material to be fermented, which has been loosened-up in this way. Clogging of the air jets is avoided by the baffles provided according to the invention.

During fermentation, gases and heat are generated which can be utilized; to this end, it is envisaged to provide the rotary drum with a central gas extraction pipe, the vacuum extraction orifice of which is above the material to be fermented and in the free part of the drum interior and in that there is associated with the gas extraction pipe a heat exchanger, a favourable energy balance being assured if there is associated with the heat exchanger an appartus for drying the fermented material after this has been discharged.

For controlling the rate of throughput, it is envisaged to associate with the rotary drum a height adjustment means for adjusting its oblique attitude. By reason of this measure, the angle of inclination of the rotary drum and thus the period of dwell of the material to be fermented can be adapted to the needs at any given time, which will be a function of the raw material.

For problem-free loading of the rotary drum, it is envisaged to associate with the feeder hopper a batch dispenser and to associate with the rotary drum a filling gate valve which can be operated by this batch dispenser. To be able easily to remove the finished fermented material from the rotary drum, it is envisaged to associate the delivery orifice with the bottom of the drum and to close it with a plough flap which can be opened out into the interior of the drum to allow delivery of the finished fermented material.

Further scope of applicability of the present invention will become apparent from the detailed description given hereinafter. However, it should be understood that the detailed description and specific examples, while indicating preferred embodiments of the invention, are given by of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENT

Figure 1:
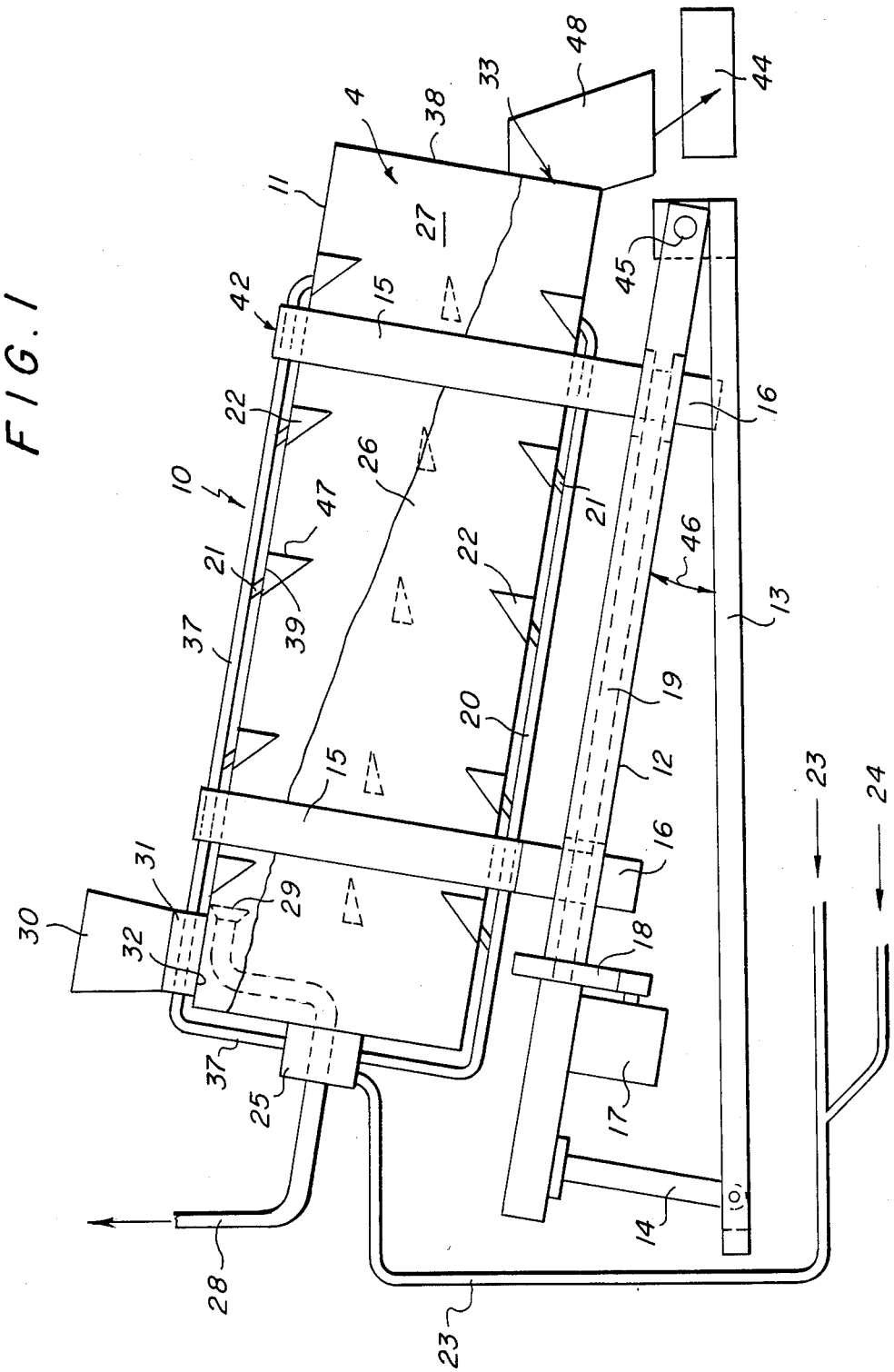
FIG. 1 is a longitudinal section through a drum reactor in the working position.

The drum reactor 10 shown in FIG. 1 consists essentially of a bottom frame 13 connected by a hinge 45 to a frame 12 on which a rotary drum 11 rests. On the side remote from the hinge 45, there is associated with the frame 12 a height adjusting device 14 by which the angle of inclination 46 relative to the bottom frame 13 can be varied.

The frame 12 is provided with rollers 16 which are rotatable transversely to the longitudinal direction of the frame. The rollers 16 are driven by a motor 17, preferably an electric motor, by a drive shaft 19 and through a gearing 18. The rotary drum 11 has distributed annularly around its periphery, drum mountings 15 by which it rests on these rollers 16. The rollers 16 and the drum mountings 15 are provided with friction linings 42 to increase traction. Thus, a rotary movement applied to the rollers 16 can easily be transmitted to the rotary drum 11.

Figure 2:
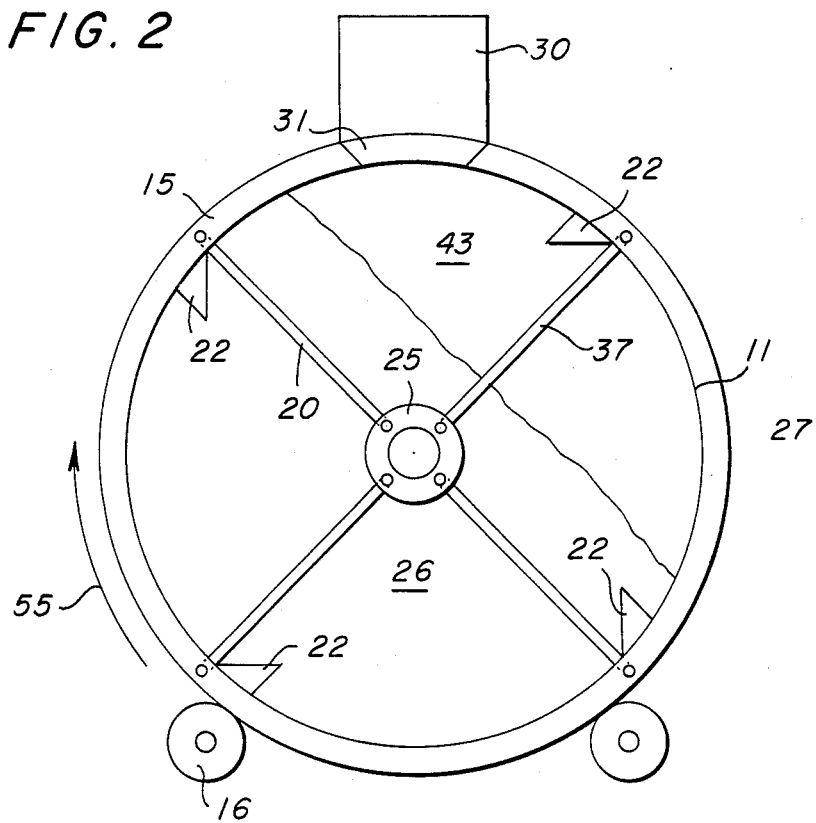
FIG. 2 is a end view of the upper end face of the rotary drum with a centrally disposed distributor gate valve and air pipes emanating from this latter.

In the case of the embodiment shown, as illustrated in FIG. 2, four air pipes 20 are disposed to extend longitudinally on and are regularly distributed around the outside of the shell of the rotary drum 11; however, as a fucntion of the drum diameter, there also may be more or fewer air pipes.

Each of these air pipes 20 is provided with a plurality of jets 21 which lead into the drum interior 27. A baffle 22 is associated with each of these jets 21 in the interior 27 of the drum. These baffles 22 are triangular in construction and are connected by a fixed side 39 to the inner wall 40 of the drum, being preferably welded thereto. They have a free side 47 which protrudes plough-like into the drum interior 27. These baffles 22 partly cover the jets 21. Their fixed side 39 is towards the upper end face 41 of the rotary drum 11 while a free side 47 points towards the drum bottom 38. These baffles 22 not only protectively mask the jets 21 but have the task, during the rotary movement of the rotary drum 11, of turning over, loosening-up and thus increasing the gas permeability of the material 26 which is being fermented. At the same time, they convey the material 26 in the direction of the drum bottom 38.

Mounted centrally on the outside of the upper drum end face 41 is a distributor gate valve 25. Leading in to this distributor gate valve 25 and coming from a compressor, not shown, there is a feed line 23 carrying air. Furthermore, the air pipes 20 associated with the rotary drum 11 converge together within it. The distributor gate valve 25 controls the supply of air to the interior of the drum so that whichever air pipe 37 is not covered by fermenting material 26 is inactive. The air is thereby forced only into the active air pipe 20 and a free and unused escape of air is avoided; thus, energy costs can be reduced considerably. Also connected to the feed line 23 is a water supply means 24 through which at the same time the necessary moisture can be introduced into the material being fermented.

Figure 3:
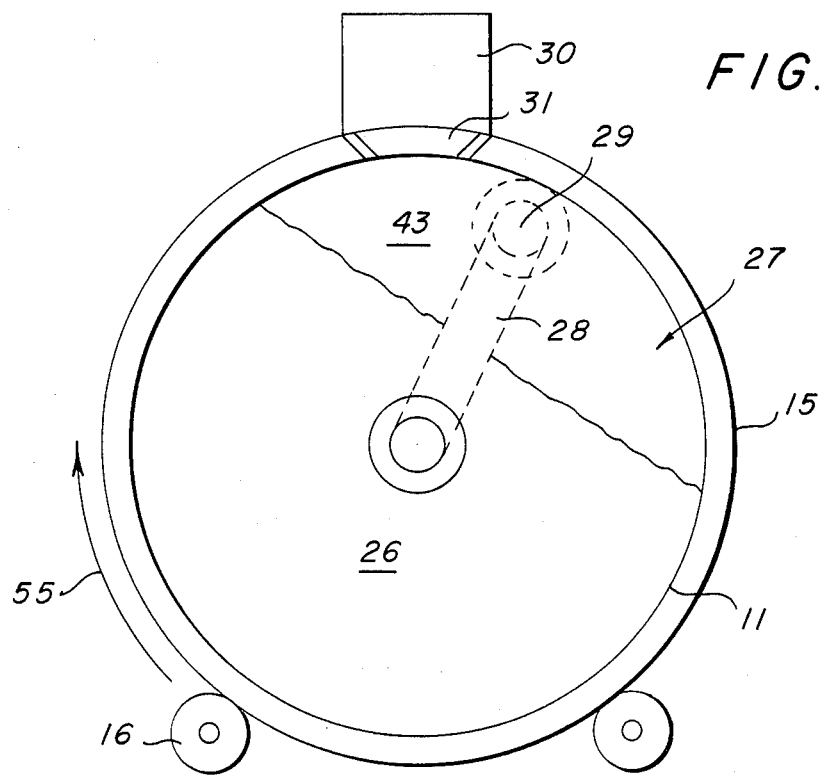
FIG. 3 is a end view similar to FIG. 2 with a centrally disposed gas extraction pipe.

As FIGS. 1 and 3 show, the extraction orifice 29 of a gas extraction pipe 28 projects into the free part 43 of the drum interior 27 above the material 26 which is being fermented. This gas extraction pipe 28 is fixed and likewise passes through the centrally disposed distributor gate valve 25.

Figure 4:
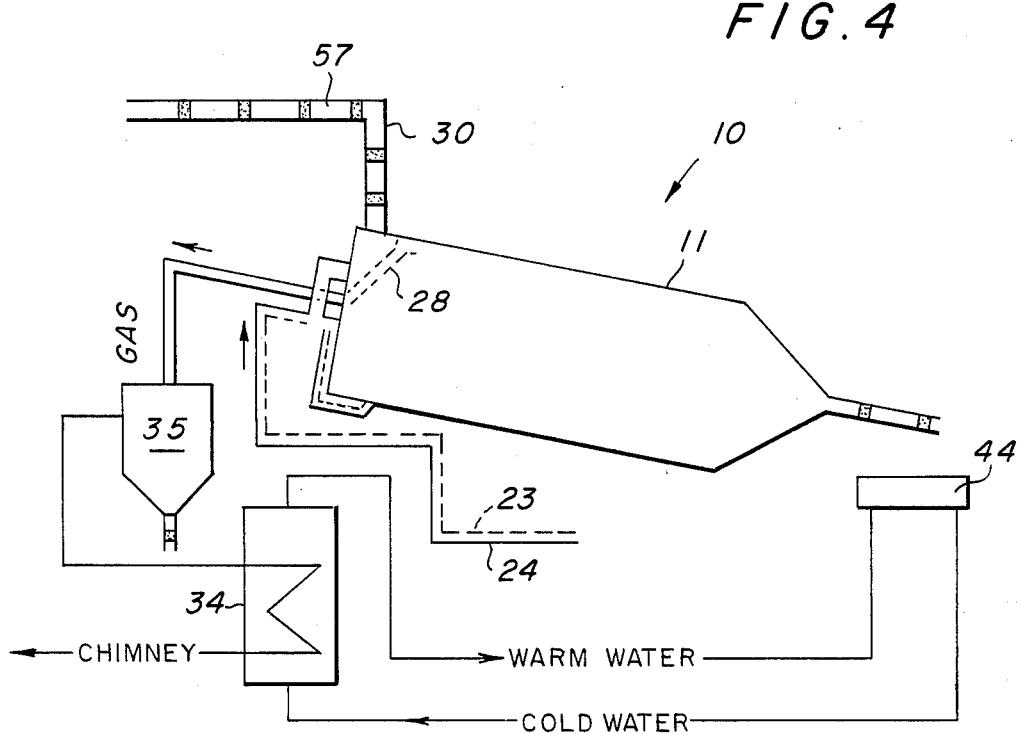
FIG. 4 is a material flow diagram for a drum reactor shown in FIG. 1.

As FIG. 4 shows, the gas extraction pipe 28 leads initially to a dust extraction plant 35 and then to a heat exchanger 34. The heat exchanger 34 heats a drying apparatus 44 for drying the completed and discharged fermented material.

The drum reactor 10 is loaded through a feeder hopper 30 which in the region of the upper drum end face 41 is rididly associated with the drum 11. The feeder hopper 30 is provided with a batch dispenser 31 shown in detail in FIGS. 5 and 6.

Figure 5:
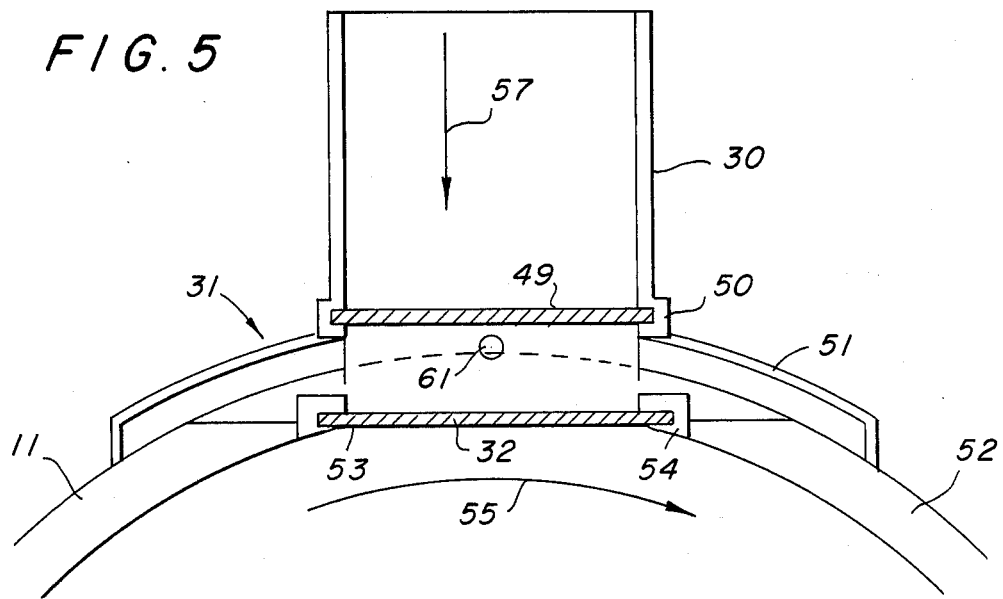
FIG. 5 is a cross-section through the feeder hopper with a batch dispenser.

The raw material 57 (arrow) is fed intermittently into the feeder hopper 30 shown in front elevation in FIG. 5. The feeder hopper is closed at the bottom by a filling gate valve 49. The filling gate valve 49 is connected to a valve drive 61 through a linkage 62. On its underside which is towards the rotary drum 11, and as shown in FIG. 6, the filling gate valve 49 is provided with, extending substantially parallel with the end face 41 of the drum, two drive plates 53 between which there is a drive gap 59.

It is possible to introduce into this drive gap 59 a flat iron member 60 which is associated with the drum gate valve 32 which is displaceable in the longitudinal direction of the rotary drum 11 in a drum slide guide 54. In the same way, the filling gate valve 49 is adapted for longitudinal displacement in a filling gate valve guide 50. If the closed rotary drum 11 is rotated in the region of the fixed feeder hopper 30, then the flat iron member 60 moves into the drive gap 59 between the inner drive plate 53 and the outer drive plate 58. The drum gate valve 32 is thus coupled to the filling gate valve 49. The linkage 62 which is only connected to the filling gate valve 49 is connected for example on its other side to a working piston 56 which runs in an hydraulically operable gate valve drive 61. The gate valve drive 61 can also be electric or pneumatic. Upon actuation of the gate valve drive 61 for the filling gate valve 49, the drum gate valve 32 is thus also moved. By this positive coupling, it is possible to save on one gate valve drive.

Once the raw material 57 present in the feeder hopper 30 has been fed into the rotary drum 11, both gate valves are closed again. The batch dispenser 31 opens up the drum gate valve 32 as a function of the level of contents in the rotary drum 11 and together with it it opens up the filling gate valve 49 when this comes into the region of the filling hopper 30 during rotation of the rotary drum 11. It closes both again when the filling gate valve 49 again leaves this zone as it continues to rotate.

Figure 6:
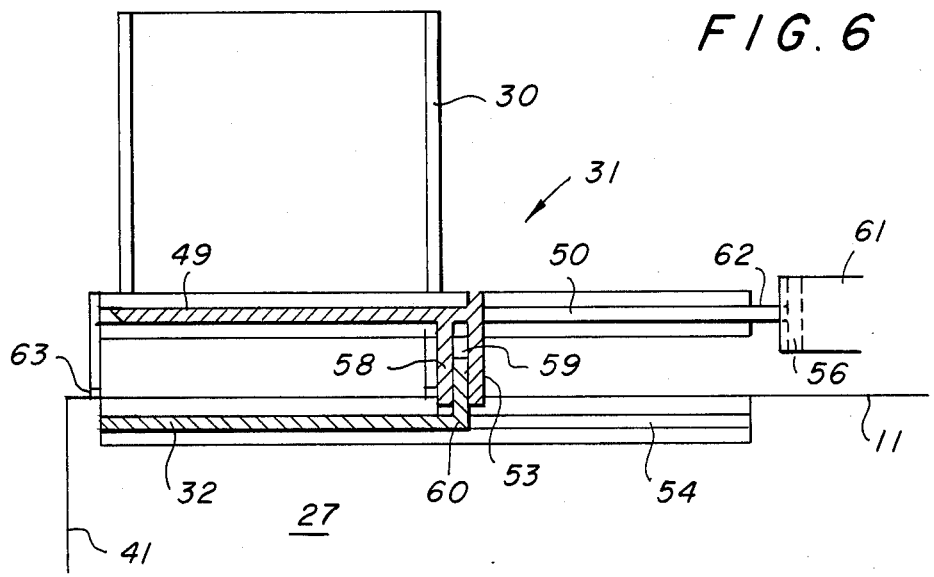
FIG. 6 is a longitudinal section through the feeder hopper with a batch dispenser according to FIG. 5.

As FIGS. 5 and 6 shows, the feeder hopper 30 is provided with a mask 51 and a seal 63 to close it off in relation to the rotary drum 11. The avoid heat losses and annoying smells, the rotary drum 11 also comprises insulation 52.

Figure 7:
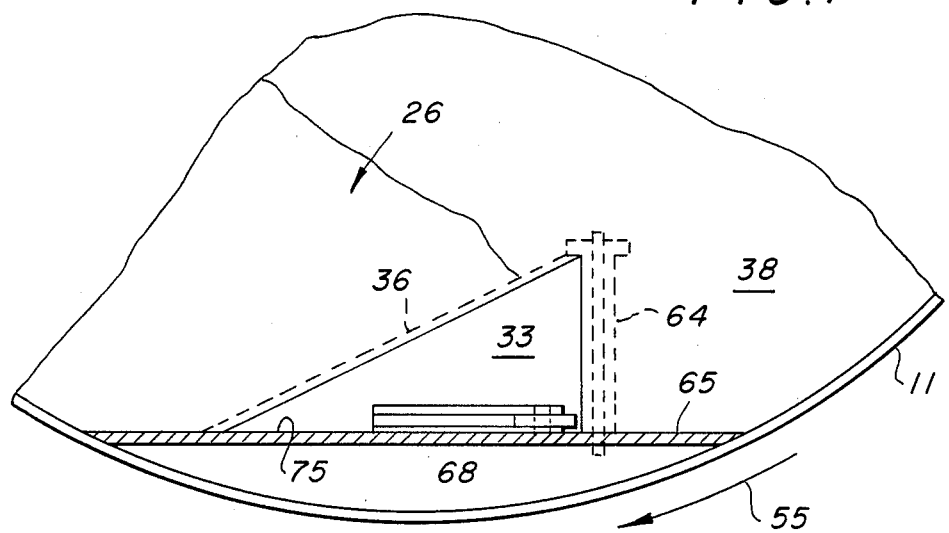
FIG. 7 is a view of the bottom of the rotary drum with a delivery orifice closed by a plough flap.

To remove the finished fermented material 26, as shown in FIG. 7, a delivery orifice 33 is provided in the bottom 38 of the drum and leads into a discharge hopper 48. The discharge orifice 33 has associated with it a plough flap 36 which closes the rotary drum 11 during fermentation.

For delivery purposes, the plough flap 36 will open out into the drum interior 27 where—due to the rotary motion 55 of the rotary drum 11—it produces a plough-like forced delivery. Disposed downstream of the discharge hopper 48 is a drying apparatus 44 with which it is possible to dry the completed and delivered fermented material.

The plough flap 36 and the discharge orifice 33 are constructed as right-angled triangles. The spindle 64 of the plough flap 36 which corresponds to the short side of a right-angle triangle is articulated on hinges 71 on the inside of the drum bottom 38. The other short side of the right-angle triangle closes off as a bottom 75 the delivery orifice 33 along a bottom plate 65 fitted tangentially of the drum periphery.

Figure 8:
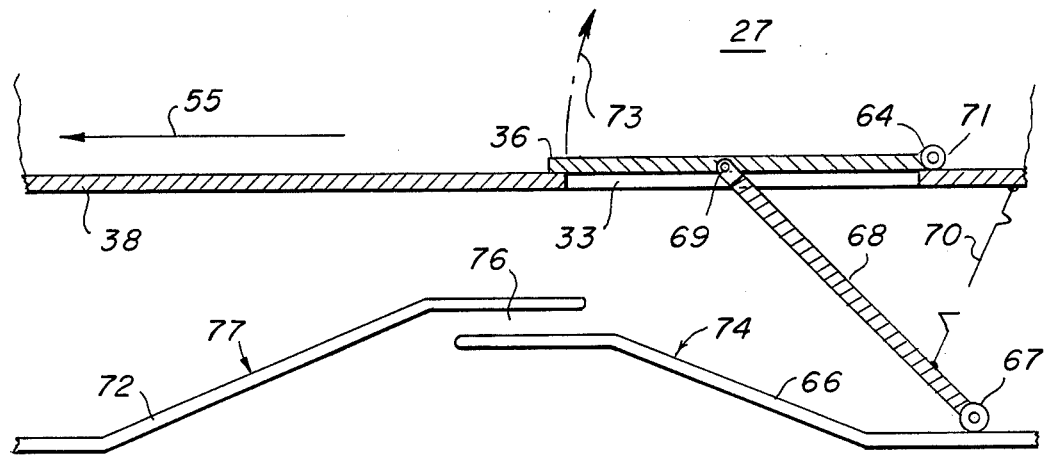
FIG. 8 is a plan view of the delivery orifice shown in FIG. 5 closed by a plough flap.
Figure 9:
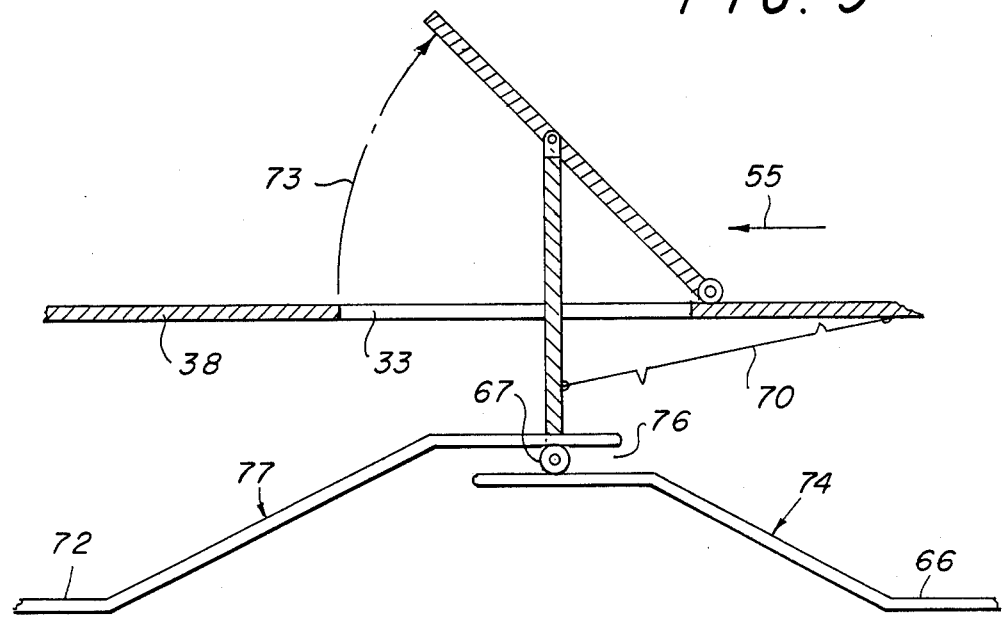
FIG. 9 is a plan view of the delivery orifice according to FIG. 6 with the plough flap open.

Associated with the plough-flap 36 is an extending lever 68 by which—as FIGS. 8 and 9 show—it is positively opened or closed again as it passes guide rails 66 and 72. FIG. 8 shows the plough flap 36 in the closed condition. For opening, the extending lever 68 which is connected by a hinge 69 to the plough flap 36 runs its guide roller 67 along a lead-in guide rail 66. In the region of the discharge orifice 33, the guide rail 66 merges into an opening path 74 which is towards the drum bottom 38 and which presses the extending lever 68 and the plough flap 36 which is connected to it along an opening angle 73 and into the rotary drum 11, as is shown in FIG. 9. The plough flap 36 is thereby opened in the rotary drum 11 in opposition to the fermenting material 26 which is moved in opposition to the direction of rotation 55. The material 26 being fermented is consequently positively discharged.

At the apex of the opening angle 73, the extending lever 68 stops for a time during which it is guided through a gap 76 which extends substantially parallel with the drum bottom 38; this results in a traction spring 70 being tensioned. In this guide gap 76, the guide roller 67 is passed to a discharge guide rail 72 which by means of the traction spring 70 closes the plough flap 36 again.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. An apparatus for manufacturing fertilizers and the like from raw materials comprising:
    a drum having a hollow interior;
    inlet means for introducing the raw materials into the interior of the drum, said drum having an upstream side near the inlet means;
    means for treating saw raw materials introduced into the drum to form said fertilizers and the like, said means for treating including fluid introduction means for introducing a fluid into the interior of the drum, said fluid aiding formation of fertilizers and the like;
    outlet means for removing the fertilizers and the like from the interior of the drum after said raw materials have been formed into said fertilizers and the like, said drum having a downstream side near the outlet means; and
    a plurality of baffles provided on the interior of the drum and operatively associated with said fluid introduction means, said baffles forming a plow-like arrangement in the interior of the drum and engaging the materials as they move from the inlet means to the outlet means while preventing the clogging of the fluid introduction means in order to aid formation of fertilizers, each of said plurality of baffles being associated with at least one of said fluid introduction means and extending over said associated fluid introduction means, each of said baffles being located on an upstream side of the associated fluid introduction means and being canted from the upstream side of the drum toward the downstream side.

2. The apparatus according to claim 1, wherein each of said plurality of baffles partially covers at least one of said fluid introduction means.

3. The apparatus according to claim 2, wherein each of said plurality of baffles is formed in the shape of a tetrahedran with a first face and a second face of each baffle facing the inlet means, a third face of each baffle facing the outlet means, and a fourth face of each baffle being adjacent the drum, said third face having an opening to permit said fluid to pass from the fluid introduction means associated with that particular baffle into the interior of the drum, said first and second faces having a common edge which is arranged to form an obtuse angle with said fourth face and which together with said first and second faces engages said materials as they move from the inlet means to the outlet means in order to stir said materials and to aid break-up of any large chunks of said material.

4. The apparatus according to claim 2, wherein said drum includes a first end near the inlet means, a second end near the outlet means and a tubular side extending between the first and second ends, said plurality of baffles with their associated fluid introduction means being arranged uniformly along the side of the drum from a position near the first end to a position near the second end of said drum.

5. The apparatus according to claim 1, wherein said fluid introduction means includes a plurality of nozzles extending into the interior of the drum, and said fluid includes at least one of air and water mist.

6. The apparatus according to claim 1, wherein said outlet means includes a plow flap which normally covers an outlet opening, said outlet opening being at an opposite end of said drum from said inlet means, and said plow flap being movable into the interior of the drum in order to permit discharge of said formed fertilizers and the like.

7. The apparatus according to claim 6, further comprising means for rotating said drum and a lever having a first end attached to said plow, further comprising a lever having a first end attached to said plow flap and a second end attached to a roller, said roller being movable along a rail means for guiding said roller as said drum is rotated, said rail means being arranged to move said roller in a direction to cause said lever to open said plow flap and permit discharge of said drum when the drum is rotated to a discharge position.

8. The apparatus according to claim 1, further comprising means for rotating said drum about its longitudinal axis, said inlet means includes a feeder hopper with a slide valve for closing one end thereof, said end being adjacent a materials inlet of said rotating drum, said slide valve comprising first and second driver plates and a drive gap, said first driver plate extends in a plane parallel to the longitudinal axis of the drum, said drum further having a flat iron member and drum gate valve at the materials inlet thereof, said drive gap receives said flat iron member as said flat iron member rotates with the drum and passes through the drive gap such that when said flat iron member is received in the drive gap and the drum is stationary, the drum gate valve may be opened to permit loading of materials into the drum.

9. Drum reactor for manufacturing fertilizers and other raw materials from waste arising from one of at least animal husbandry, plant residues and other fermentable raw materials by aerobic fermentation, said drum reactor comprising:
    a feed hopper;
    a rotary drum having a hollow interior and a first and second end, said drum being adapted to hold the materials to be fermented and being capable of rotating about a longitudinal axis extending through said first and second ends, said drum receiving said materials from said feeder hopper whereafter said materials move toward an outlet in the second end of the drum;
    a plow flap for closing said outlet, said plow flap being moveable into the interior of the drum in order to permit discharge of finished fermented materials;

a plurality of pipes extending along the outside of the drum, each of said pipes having a portion which is parallel to the longitudinal axis of the drum;

a plurality of nozzles being provided along said portions of each of said pipes, said nozzles extending into the interior of the drum and permitting the injection of a gas into the interior of the drum; and a plurality of baffles being provided on the interior of the drum, each baffle partially covering at least one of the nozzles, said baffles forming a plow-like arrangement in the interior of the drum and engaging the materials as they move from the first to the second end of the drum in order to aid fermentation.

10. The drum reactor according to claim 9, wherein said gas is air.

11. The drum reactor according to claim 9, wherein said outlet has a batch dosing unit and the rotary drum has a feeder gate valve that can be actuated by said batch dosing unit.

12. The drum reactor according to claim 9, further comprising a lever having a first end attached to said plow flap and a second end attached to a roller, said roller being movable along a rail means for guiding said roller as said drum is rotated, said rail means being arranged to move said roller in a direction to cause said lever to open said plow flap and permit discharge of said drum when the drum is rotated to a discharge position.

13. The drum reactor according to claim 9, further comprising a central gas suction pipe having an intake orifice, said suction pipe extends into the interior of the drum and enables withdrawal of gas contained therein, said orifice being positioned so as to be well above the level of the materials in the drum.

14. The drum reactor according to claim 13, wherein a heat exchanger is provided for said suction pipe, said heat exchanger having a drying unit which aids drying of the fermented materials discharged from the drum.

15. The drum reactor according to claim 9, further comprising roller means for permitting rotation of said drum.

16. The drum reactor according to claim 9, wherein the feeder hopper has a slide valve for closing one end thereof, said end being adjacent a materials inlet of said rotating drum, said slide valve comprising first and second driver plate and a drive gap, said first driver plate extends in a plane parallel to the longitudinal axis of the drum, said drum further having a flat iron member and drum gate valve at the materials inlet thereof, said drive gap receives said flat iron member as said flat iron member rotates with the drum and passes through the drive gap such that when said flat iron member is received in the drive gap and the drum is stationary, the drum gate valve may be opened to permit loading of materials into the drum.

17. A method for manufacturing fertilizers and other raw materials from waste arising from one of at least animal husbandry, plant residues and other fermentable raw materials by aerobic fermentation, said method comprising the steps of:

placing said materials in a feed hopper adjacent a rotatable drum, said feed hopper having a slide valve with a first and second drive plate thereon, said slide valve being moveable between an open and closed position to open and close an outlet in said feed hopper;

rotating said drum to position a flat iron member thereon between said first and second drive plates, said flat iron member being attached to a drum gate valve, said drum gate valve being moveable between an open and closed position to open and close an outlet on said drum;

moving said slide valve to said open position;

simultaneously moving said drum gate valve to said open position as said slide valve is opened, said drum gate valve being moved via said first and second drive plates moving said flat iron member as said slide valve is opened;

discharging said materials from the feed hopper to the drum through said drum inlet in response to said slide valve and said drum gate valve moving to said open position;

moving said slide valve to said closed position after said discharging;

simultaneously moving said drum gate valve to said closed position as said slide valve is closed, said drum gate valve being moved via said first and second drive plates moving said flat iron member as said slide valve is closed;

rotating the drum with the materials while injecting one of at least air and water into the drum to permit fermentation;

moving the materials from an end of the drum at which they were inserted to a second end during rotation of the drum, said materials engaging plow-like baffles during said moving from one end of the drum to the other, said engaging of said baffles aiding fermentation of the materials; and discharging the materials from the second end of the drum after they have finished fermenting.

18. Drum reactor for manufacturing fertilizers and other raw materials from waste arising from one of at least animal husbandry, paint residues and other fermentable raw materials by aerobic fermentation, said drum reactor comprising:

a feeder hopper;

a rotary drum having a hollow interior and a first and second end, said drum being adapted to hold the materials to be fermented and being capable of rotating about a longitudinal axis extending through said first and second ends, said drum receiving said materials from said feeder hopper whereafter said materials move toward an outlet in the second end of the drum;

a plurality of pipes extending along the outside of the drum, each of said pipes having a portion which is parallel to the longitudinal axis of the drum;

a water supply inlet for said plurality of pipes;

a plurality of nozzles being provided along said portions of each of said pipes, said nozzles extending into the interior of the drum and permitting the injection of at least one of a gas and fluid into the interior of the drum; and a plurality of baffles being provided on the interior of the drum, each baffle partially covering at least one of the nozzles, said baffles forming a plow-like arrangement in the interior of the drum and engaging the materials as they move from the first to the second end of the drum in order to aid fermentation.

* * * * *